United States Patent
Konofagou et al.

(10) Patent No.: US 12,369,880 B2
(45) Date of Patent: Jul. 29, 2025

(54) SYSTEMS AND METHODS FOR BLOOD-BRAIN BARRIER OPENING AND CAVITATION IMAGING USING A DIAGNOSTIC IMAGING ARRAY

(71) Applicant: THE TRUSTEES OF COLUMBIA UNIVERSITY IN THE CITY OF NEW YORK, New York, NY (US)

(72) Inventors: Elisa E. Konofagou, New York, NY (US); Mark Burgess, Ramsey, NJ (US); Robin Ji, New York, NY (US); Alec J. Batts, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 18/166,615

(22) Filed: Feb. 9, 2023

(65) Prior Publication Data
US 2023/0181149 A1    Jun. 15, 2023

Related U.S. Application Data

(63) Continuation of application No. PCT/US2021/045939, filed on Aug. 13, 2021.
(Continued)

(51) Int. Cl.
*A61B 8/06* (2006.01)
*A61B 8/08* (2006.01)
(Continued)

(52) U.S. Cl.
CPC .............. *A61B 8/06* (2013.01); *A61B 8/0808* (2013.01); *A61B 8/488* (2013.01); *A61N 2007/0039* (2013.01)

(58) Field of Classification Search
CPC ......... A61B 8/06; A61B 8/0808; A61B 8/488; A61N 2007/0039
See application file for complete search history.

(56) References Cited

U.S. PATENT DOCUMENTS

| 8,235,901 B2 | 8/2012 | Schmidt et al. |
| 10,596,362 B2 | 3/2020 | Fielder et al. |
(Continued)

FOREIGN PATENT DOCUMENTS

| JP | A-2004-113608 A | 4/2004 |
| JP | A-2018-122082 A | 8/2018 |
(Continued)

OTHER PUBLICATIONS

Ali et al.; "The promising shadow of microbubble over medical sciences: from fighting wide scope of prevalence disease to cancer eradication"; Jangiou et al. J Biomed Sci (2021) 28:49 (Year: 2021).*
(Continued)

*Primary Examiner* — Dixomara Vargas
(74) *Attorney, Agent, or Firm* — Baker Botts L.L.P.

(57) ABSTRACT

The present subject matter relates to techniques for simultaneous blood-brain barrier opening and cavitation imaging. The disclosed system can include a transducer and a processor. The transducer can be configured to generate a plurality of focused transmits and simultaneously obtain a plurality of power cavitation images. The processor can be configured to control a parameter of the focused transmits, acquire the power cavitation images between each focused transmit, and generate a cavitation map based on the power cavitation images.

19 Claims, 5 Drawing Sheets

Related U.S. Application Data (60) Provisional application No. 63/065,319, filed on Aug. 13, 2020.

(51) Int. Cl.
 *A61B 8/00* (2006.01)
 *A61N 7/00* (2006.01)

(56) References Cited

U.S. PATENT DOCUMENTS

| | | | |
|---|---|---|---|
| 10,653,387 | B2 | 5/2020 | Tanter et al. |
| 2017/0307742 | A1 | 10/2017 | Hope Simpson et al. |
| 2018/0140871 | A1 | 5/2018 | Konofagou et al. |
| 2019/0030374 | A1 | 3/2019 | Carpentier et al. |
| 2019/0083065 | A1* | 3/2019 | Vitek .................. A61B 8/0808 |
| 2019/0175954 | A1* | 6/2019 | Levy .................... A61B 8/585 |
| 2019/0184204 | A1 | 6/2019 | Ramamurthy |
| 2019/0192112 | A1 | 6/2019 | Konofagou et al. |
| 2020/0086146 | A1 | 3/2020 | Konofagou et al. |
| 2021/0212709 | A1* | 7/2021 | Pernot ................. A61B 8/5269 |

FOREIGN PATENT DOCUMENTS

| | | |
|---|---|---|
| JP | A-2019-535448 A | 12/2019 |
| WO | WO 2019/069135 A1 | 4/2019 |

OTHER PUBLICATIONS

Vasant et al.; "Passive cavitation imaging with ultrasound arrays"; J. Acoust. Soc. Am. 126 (6), Dec. 2009. pp. 3071-3083 (Year: 2009).*

Abrahao et al., "First-in-human trial of blood-brain barrier opening in amyotrophic lateral sclerosis using MR-guided focused ultrasound," Nat Commun., 10(1):4373 (2019).

Assistance Publique—Hôpitaux de Paris, "Safety of BBB Opening with the SonoCloud," Clinical Trial #: NCT02253212 (2014).

Burgess et al., "Power cavitation-guided blood-brain barrier opening with focused ultrasound and microbubbles," Phys Med Biol., 63(6): 065009 (2019).

Butts-Pauly, "The Impact of FUS-Mediated Brain Cancer Therapy on BBB Transport, Cytokines, and Immunocyte Trafficking," NIH Grant #: 1R01CA227687-01 (2018).

Çavuşoğblu et al., "Closed-loop cavitation control for focused ultrasound-mediated blood-brain barrier opening by long-circulating microbubbles," Physics in Medicine and Biology, 64(4): 045012 (2019).

Idbaih et al., "Safety and Feasibility of Repeated and Transient Blood-Brain Barrier Disruption by Pulsed Ultrasound in Patients with Recurrent Glioblastoma," Clinical Cancer Research, (13):3793-3801 (2019).

Imbault et al., "Intraoperative functional ultrasound imaging of human brain activity," Scientific Reports, 4;7(1):7304 (2017).

International Search Report and Written Opinion mailed Nov. 23, 2021 corresponding to International Patent application No. PCT/US2021/045939.

Pouliopoulos et al., "A clinical system for non-invasive blood-brain barrier opening using a neuronavigation-guided single-element focused ultrasound transducer" vol. 45, No. 1, 73-89 (2019).

Yuan et al., Macrophage exosomes as natural nanocarriers for protein delivery to inflamed brain, Biomaterials, 142, 1-12 (2017).

Extended European Search Report dated Dec. 22, 2023 in Application No. EP 21856788.

Ji et al., "Transcranial Blood-Brain Barrier Opening and Power Cavitation Imaging Using a Diagnostic Imaging Array," 2019 IEEE International Ultrasonics Symposium (IUS), IEEE, Oct. 6, 2019, pp. 2-4.

Pouliopoulos et al., "Doppler Passive Acoustic Mapping," IEEE Transactions On Ultrasonics, Ferroelectrics, And Frequency Control, 67(12):2692-2703 (2020).

* cited by examiner

SYSTEMS AND METHODS FOR BLOOD-BRAIN BARRIER OPENING AND CAVITATION IMAGING USING A DIAGNOSTIC IMAGING ARRAY

CROSS-REFERENCE TO RELATED APPLICATION

This application is a continuation of International Patent Application No. PCT/US2021/045939, filed on Aug. 13, 2021, which claims priority to U.S. Provisional Patent Application No. 63/065,319, which was filed on Aug. 13, 2020, the entire contents of which are incorporated in their entirety, and to each of which priority is claimed.

GRANT INFORMATION

This invention was made with government support under grant numbers R01EB009041, R01EB029338, and R01AG038961, awarded by the National Institutes of Health (NIH). The government has certain rights in the invention.

BACKGROUND

Focused-ultrasound (FUS) mediated blood-brain barrier (BBB) opening can be used to noninvasively deliver drugs to the central nervous system (CNS). Certain FUS systems for opening the BBB require custom-built geometrically focused transducers with a fixed focal point or a very complex and large multi-element array system. Such transducers can have limited focusing capabilities, be expensive and/or cumbersome to use. For example, certain clinical trials have required magnetic resonance imaging (MRI) guidance for proper targeting and monitoring.

Furthermore, certain FUS transducers can target a single location at a time and has to be physically translated in order to target other regions. Due to the therapy time, ultrasound transducer movements, and microbubble clearance, reinjections can be required if multiple targets are necessary. Also, these transducers can provide insufficient spatial information of microbubble cavitation during the therapy.

Therefore, there is a need for an improved ultrasound technique that can utilize diagnostic ultrasound systems for simultaneous blood-brain barrier (BBB) opening and cavitation imaging.

SUMMARY

The disclosed subject matter provides techniques for simultaneous blood-brain barrier opening and cavitation imaging.

An exemplary system can include a transducer and a processor. The transducer can be configured to generate a plurality of focused transmits and simultaneously obtain a plurality of power cavitation images. The processor can be configured to control a parameter of the focused transmits, acquire the power cavitation images between each focused transmit, and generate a cavitation map based on the power cavitation images.

In certain embodiments, the system can include a plurality of microbubbles. In non-limiting embodiments, a size of the microbubbles can range from about 1 micron to about 10 microns.

In certain embodiments, the plurality of focused transmits can include a focal depth between about 1 mm to about 100 mm. In non-limiting embodiments, the plurality of focused transmits can include a steering angle between about 0° to about 360°. In non-limiting embodiments, the plurality of focused transmits can include a pulse length between about 1 cycle to about 2500 cycles. In non-limiting embodiments, the plurality of focused transmits can include a center frequency between about 1.5 MHz to 3.5 MHz. In non-limiting embodiments, the plurality of focused transmits can include a pulse repetition frequency between about 100 Hz to about 1000 Hz.

In certain embodiments, the processor can be configured to adjust the parameter of each focused transmit to target multiple areas. In non-limiting embodiments, the parameter can include a steering angle, a focal depth, a pulse length, a center frequency, a pulse repetition frequency, and combinations thereof.

In certain embodiments, the processor can be configured to perform microbubble power Doppler imaging. In non-limiting embodiments, the transducer can be configured to acquire microbubble power doppler images using a plane imaging wave between each of the focused transmit. In non-limiting embodiments, the size of the microbubbles can range from about 1 micron to about 10 microns.

In certain embodiments, the processor can be configured to perform beamforming on the acquired images, accumulate beamformed images, and spatiotemporally filter the beamformed images using a singular value decomposition filter.

The disclosed subject matter also provides methods for simultaneous blood-brain barrier opening and cavitation imaging. An example method can include generating a plurality of focused transmits using a therapeutic transducer, simultaneously obtaining a plurality of power cavitation images using the therapeutic transducer, and generating a cavitation map based on the power cavitation images. The power cavitation images can be obtained between each focused transmit.

In certain embodiments, the method can further include adjusting the parameter of each focused transmit. In non-limiting embodiments, the parameter can include a steering angle, a focal depth, a pulse length, a center frequency, a pulse repetition frequency, or combinations thereof.

In certain embodiments, the method can include introducing microbubbles and performing microbubble power Doppler imaging by acquiring microbubble power doppler images with a plane imaging wave between each of the focused transmit.

In certain embodiments, the method can further include performing beamforming on the acquired images, accumulating beamformed images, and spatiotemporally filtering the beamformed images using a singular value decomposition filter.

The disclosed subject matter will be further described below.

It is to be understood that both the foregoing general description and the following detailed description are exemplary and are intended to provide further explanation of the disclosed subject matter.

DETAILED DESCRIPTION

The disclosed subject matter provides techniques for simultaneous blood-brain barrier (BBB) opening and cavitation imaging. The disclosed subject matter provides systems and methods for BBB opening and cavitation imaging using a single diagnostic transducer.

The terms "comprise(s)," "include(s)," "having," "has," "can," "contain(s)," and variants thereof, as used herein, are intended to be open-ended transitional phrases, terms, or words that do not preclude additional acts or structures. The singular forms "a," "an," and "the" include plural references unless the context clearly dictates otherwise. The present disclosure also contemplates other embodiments "comprising," "consisting of," and "consisting essentially of," the embodiments or elements presented herein, whether explicitly set forth or not.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and up to 1% of a given value. Alternatively, e.g., with respect to biological systems or processes, the term can mean within an order of magnitude, within 5-fold, and within 2-fold, of a value.

The term "coupled," as used herein, refers to the connection of a device component to another device component by methods known in the art.

As used herein, the term "subject" includes any human or nonhuman animal. The term "nonhuman animal" includes, but is not limited to, all vertebrates, e.g., mammals and non-mammals, such as nonhuman primates, dogs, cats, sheep, horses, cows, chickens, amphibians, reptiles, etc.

In certain embodiments, the disclosed subject matter provides a system for simultaneous BBB opening of a subject and cavitation imaging. An example system can include a transducer and a processor. In certain embodiments, the processor can be operatively coupled to the transducer. For example, the processor and the transducer can be coupled directly (e.g., wire connection or installation into the transducer) or indirectly (e.g., wireless connection).

In certain embodiments, the transducer can be a single transducer that can be configured to generate a plurality of focused transmits and simultaneously obtain a plurality of power cavitation images. In non-limiting embodiments, a transmit can be electronically exciting a piezoelectric element within a transducer. The transmit can include the excitation of a single element, a subgroup of elements, or all the elements in the transducer. Transmits can be induced by simultaneously exciting all or a subgroup of elements, or consecutively exciting individual elements at a predefined interval. In non-limiting embodiments, the transmit can be a focused ultrasound (FUS) transmit. The transducer can be used to open the target tissue of a subject by inducing cavitation of microbubbles. For example, the disclosed transducer can generate microbubble cavitation at the BBB of a subject to open the BBB by applying the disclosed transmits. In some embodiments, the FUS-induced microbubbles cavitation can open target tissue without permanent damaging/heating the target tissue. In non-limiting embodiments, damage/heating of target tissue can be achieved through adjustment of the transmit parameters (e.g., peak negative pressure, pulse length, sonication duration).

In certain embodiments, the disclosed system can include microbubbles. The microbubbles can be configured to react to a predetermined pulse of the FUS and induce cavitation for opening the target tissue. The size of the microbubbles can range from about 1 micron to about 10 microns, from about 1 micron to about 9 microns, from about 1 micron to about 8 microns, from about 1 micron to about 7 microns, from about 1 micron to about 6 microns, from about 1 micron to about 6 microns, from about 1 micron to about 5 microns, from about 2 microns to about 5 microns, from about 3 microns to about 5 microns, or from about 4 microns to about 5 microns. In non-limiting embodiments, the size of the microbubbles can be about 4 microns or about 5 microns. In some embodiments, the dose of the microbubbles can be adjusted depending on the subject. For example, clinical doses (e.g., about 10 μl/kg) of the microbubbles for ultrasound imaging applications can be administered to a human subject.

In certain embodiments, the microbubbles are configured to carry or be coated with an active agent. The microbubbles can be configured to carry an active agent (e.g., small molecule) and be acoustically activated. For example, the molecule-carrying microbubbles can carry or be coated with medicinal molecules and/or a contrast agent and/or a biomarker and/or a liposome. Medicinal molecules and/or contrast agents can also be separately positioned in proximity to the targeted region.

In certain embodiments, the disclosed transducer can be configured to simultaneously perform cavitation imaging while inducing the transmits to open the target tissue. In non-limiting embodiments, the disclosed transducer can perform power cavitation imaging. For example, the disclosed transducer can obtain power cavitation images between each of the focused transmits. Power cavitation imaging (PCI) can be the detection/imaging of microbubble cavitation by the same transducer in response to the focused transmits used to open the target tissue. The detected microbubble cavitation can be processed through ultrasound beamforming to generate a power cavitation image. In non-limiting embodiments, the raw frames/images can be accumulated before sending to the processor. In non-limiting embodiments, the power cavitation images can be used for estimating the size of the focus in the imaging plane.

In certain embodiments, the disclosed transducer can be configured to perform microbubble power Doppler imaging. Microbubble power doppler images can be acquired using a high frame rate plane wave between each of the focused transmits. For example, power doppler images can be acquired using a high frame rate plane-wave compounding for a predetermined amount of compounded frames. Compounding can be the accumulation or averaging of multiple ultrasound frames acquired consecutively at varying plane-wave transmit angles into a single image. The high frame rate plane-wave compounding can have about 1, about 2, about 3, about 4, about 5, about 6, about 7, about 8, about 9, or about 10 angles. The high frame rate plane-wave compounding can have a frequency between about 100 Hz, 200 Hz, 300 Hz, 400 Hz, 500 Hz, 600 Hz, 700 Hz, 800 Hz, 900 Hz, 1000 Hz, 1500 Hz, 2000 Hz, 2500 Hz, 3000 Hz, 3500 Hz, 4000 Hz, 4500 Hz, or 5000 Hz. In non-limiting embodiments, the predetermined amount of the compounded frames can be at least about 50, at least about 100, at least about 150, at least about 200, at least about 250, or at least about 300.

In certain embodiments, the disclosed system can include a processor coupled to the transducer. The processor can be configured to perform the instructions specified by software stored in a hard drive, a removable storage medium, or any other storage media. The software can include computer codes, which can be written in a variety of languages, e.g., MATLAB and/or Microsoft Visual C++. Additionally or alternatively, the processor can include hardware logic, such as logic implemented in an application-specific integrated circuit (ASIC). The processor can be configured to control one or more of the system components described above. For example, and as embodied herein, the processor can be configured to control the operation of the transducer.

In certain embodiments, the processor can be configured to control a parameter of the transmit that is induced by the disclosed transducer. The parameter can include a steering angle, a focal depth, a pulse length, a transmit frequency, a pulse repetition frequency, a burst repetition frequency, or combinations thereof.

In non-limiting embodiments, the center frequency of the transmit can range from about 1 megahertz (MHz) to about 10 MHz, from about 1 MHz to about 5 MHz, from about 1 megahertz (MHz) to about 3.5 MHz, from about 1.5 megahertz (MHz) to about 3.5 MHz, from about 2.5 megahertz (MHz) to about 3.5 MHz, or from about 0.25 megahertz (MHz) to about 1.5 MHz.

In non-limiting embodiments, a pulse repetition frequency (PRF) of the transmit can range from about 10 Hz to about 5000 Hz, from about 10 Hz to about 1500 Hz, from about 10 Hz to about 1000 Hz, from about 50 Hz to about 1000 Hz, or from about 100 Hz to about 1000 Hz.

In non-limiting embodiments, a focal depth of the transmit can range from about 1 mm to about 1000 mm, from about 1 mm to about 500 mm, from about 1 mm to about 250 mm, from about 1 mm to about 100 mm, from about 1 mm to about 90 mm, from about 1 mm to about 80 mm, from about 1 mm to about 70 mm, from about 1 mm to about 60 mm, from about 1 mm to about 50 mm, from about 1 mm to about 40 mm, from about 1 mm to about 30 mm, from about 1 mm to about 20 mm, or from about 1 mm to about 10 mm.

In non-limiting embodiments, a pulse length of the transmit can be at least about 2 cycles, at least about 20 cycles, at least about 30 cycles, at least about 40 cycles, or at least about 50 cycles. The pulse length can also range from about 1 cycle to about 5000 cycles, from about 1 cycle to about 4000 cycles, from about 1 cycle to about 3000 cycles, from about 1 cycle to about 2500 cycles, from about 500 cycles to about 2500 cycles, from about 1000 cycles to about 2500 cycles, from about 1500 cycles to about 2500 cycles, or from about 2000 cycles to about 2500 cycles. The pulse length can range from about 1 millisecond (ms) to about 100 ms, from about 1 ms to about 90 ms, from 1 ms to about 80 ms, from 1 ms to about 70 ms, from 1 ms to about 60 ms, from 1 ms to about 50 ms, from 1 ms to about 40 ms, from 1 ms to about 30 ms, from 1 ms to about 20 ms, from 1 ms to about 10 ms, from 2 ms to about 10 ms, from 3 ms to about 10 ms, from 4 ms to about 10 ms, or from 5 ms to about 10 ms.

In non-limiting embodiments, the steering angle of the transmit can range from about 0° to about 90°.

In certain embodiments, the processor can be configured to control a parameter of the transducer for obtaining power cavitation images and/or microbubble power doppler images. The processor can transmit the focused transmits to a specified target region within the tissue and acquire the cavitation response through the focused transmits (e.g., transmit frequency: 1.5 MHz, pulse length: 3-5 cycles, pulse repetition frequency: 1000 Hz, number of pulses per burst: 100, and burst repetition frequency: 0.5 Hz). The acquired cavitation signal can be beamformed to generate power cavitation images and accumulate over the duration of the therapy. Beamformed power cavitation images can be further filtered using a spatiotemporal clutter filter to isolate microbubble cavitation. In non-limiting embodiments, microbubble power doppler images can be additionally acquired on their own or sequentially after power cavitation imaging. The processor can transmit high frame rate plane-wave compounding to insonify all the microbubbles in the processor's field of view (e.g., transmit frequency: 1.5 MHZ, pulse length: 3 cycles, pulse repetition frequency: 2500 Hz, number of angles: 5, angle range: from −6 degrees to +6 degrees, and number of compounded frames: 500). The acquired power doppler images can be beamformed and filtered using a spatiotemporal clutter filter in order to isolate microbubble cavitation.

In certain embodiments, the processor can be configured to acquire the power cavitation/microbubble power doppler images between each focused transmit. For example, the raw frames/images between each focused transmit can be obtained by the disclosed transducer and be accumulated before sending to the processor. The processor can receive the accumulated images. In non-limiting embodiments, the processor can be configured to generate beamformed images by performing delay-and-sum beamforming on the received images. For example, a custom delay-and-sum beamforming can be applied to the channel data to construct beamformed radiofrequency (RF) data/images. The processor can further accumulate the beamformed images and spatiotemporally filter the beamformed images using a singular value decomposition filter. In non-limiting embodiments, the processor can be configured to generate a cavitation map based on the obtained images. The cavitation maps can signify the location of microbubble cavitation within the target tissue and the location where bioeffects can occur within the target tissue. In non-limiting embodiments, the cavitation maps can be generated through the accumulation of the spatiotemporally filtered beamformed images acquired during the acquisition.

In certain embodiments, the target tissue can be any tissue. For example, the target tissue can be a brain, muscle, tendons, ligaments, skin, vessels, artery, arterial tissue, renal tissue, or a combination thereof.

In certain embodiments, the disclosed subject matter provides a method for simultaneous blood-brain barrier opening and cavitation imaging. An example method can include generating a plurality of focused transmits using a therapeutic transducer, simultaneously obtaining a plurality of power cavitation images using the therapeutic transducer, and generating a cavitation map based on the power cavitation images. In non-limiting embodiments, the power cavitation images can be obtained between each focused transmit.

In certain embodiments, the disclosed method can further include adjusting the parameter of each focused transmit. The parameter can include a steering angle, a focal depth, a pulse length, a center frequency, a pulse repetition frequency, or combinations thereof. For example, a single diagnostic linear array (e.g., Bandwidth: 1.5 MHz-3.5 MHz, Number of elements: 96) with ultrasound parameters for both FUS-mediated BBB opening and cavitation monitoring. Using electronic delays, the ultrasound can be focused at different depths (axial steering) and steered at different angles (lateral steering). In non-limiting embodiments, the disclosed transducer mediated BBB opening can be performed using focused pulses transmitted at a pulse repetition frequency (PRF) of 1,000 Hz for 100 pulses. For example, the burst of 100 focused pulses can be transmitted and received for BBB opening and power cavitation imaging. This burst of 100 focused pulses can be transmitted at a predetermined frequency (e.g., every 2 seconds) for a burst repetition frequency (e.g., 0.5 Hz). Through the disclosed processor, custom parameters for each focused pulse can be programmed.

In non-limiting embodiments, all focused pulses can be transmitted using the same center frequency, focusing depth, and steer angle, resulting in a single location of BBB opening. In non-limiting embodiments, the parameters for the focused pulses can be individually adjusted in order to target multiple areas by alternating between different parametric cases. For example, the left hemisphere and right hemisphere of a subject can be targeted by adjusting the steering angle for every other transmit sequence, such that half of the focused pulses can be transmitted to the left hemisphere, and half of the focused pulses can be transmitted to the right hemisphere, in an alternating fashion. This can be further extended to also include different pulses lengths or focal depths as well. This allows for multiple targets of BBB opening in a single shot without requiring microbubble reinjection or physical translation of the ultrasound transducer. The disclosed subject matter can allow consistent BBB opening in multiple targets with a single injection of microbubbles.

In certain embodiments, the disclosed method can further include introducing microbubbles and performing microbubble power Doppler imaging by acquiring microbubble power doppler images with a plane imaging wave between each of the focused transmit. For example, power cavitation imaging (PCI) and microbubble power Doppler imaging (PDI) can be performed using the disclosed transducer. In addition to the cavitation signals acquired from each focused transmit, microbubble power doppler images can be acquired using high frame rate plane wave imaging between each focused transmit burst. For example, power doppler images can be acquired using high frame rate plane-wave compounding (e.g., 5 angles, 2,500 Hz), for a total of 100 compounded frames and an effective rate of about 500 Hz.

In certain embodiments, the disclosed method can further include performing beamforming on the acquired images, accumulating beamformed images, and spatiotemporally filtering the beamformed images using a singular value decomposition filter. For example, channel data/images can be acquired both for PCI and PDI and be beamformed using a delay-and-sum (DAS) beamforming algorithm. The ensemble of beamformed frames can be accumulated over time and then spatiotemporally filtered using a singular value decomposition (SVD) filter. The SVD filter can remove stationary reflections (e.g., skull reflection) and slow-moving flow (e.g., tissue movement). Afterward, the power of the respective SVD filtered images can be taken to generate a single PCI frame and PDI frame, providing spatial information on where microbubble cavitation during BBB opening occurred (PCI) as well as the location of all the microbubbles currently present in the brain (PDI).

EXAMPLES

Figure 5:
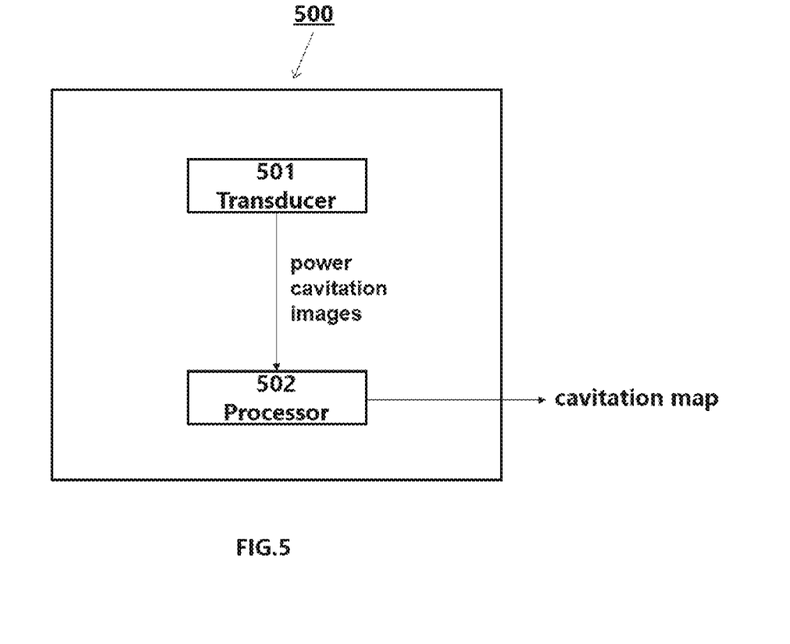
FIG. 5 provides a diagram showing the system for simultaneous blood-brain barrier opening and cavitation imaging in accordance with the disclosed subject matter.

Example 1: Blood-Brain Barrier Opening and Power Cavitation Imaging Using a Diagnostic Imaging Array Certain focused ultrasound (FUS)-mediated blood-brain barrier (BBB) opening techniques require multiple components that include the therapeutic transducer itself and a separate monitoring device. Combining the therapeutic transducer and monitoring technique into a single transducer can be challenging. The disclosed subject matter provides systems and techniques, which can utilize a single diagnostic array for both FUS-mediated BBB opening and cavitation monitoring. Referring to FIG. 5, an example system 500 for simultaneous blood-brain barrier opening and cavitation imaging can include a transducer 501 and a processor 502. In certain embodiments, the disclosed system 500 can use a diagnostic transducer to obtain power cavitation images during focus transmits. These power cavitation images can be used to estimate the size of the focus in the imaging plane, which can match well with the measurements taken with a hydrophone. Furthermore, the disclosed subject matter can provide successful transcranial BBB opening and cavitation monitoring in mice and non-human primates animal models. BBB opening can be further confirmed using contrast-enhanced magnetic resonance imaging, which can be correlated well with the corresponding power cavitation maps showing high cavitation activity.

Figure 1A:
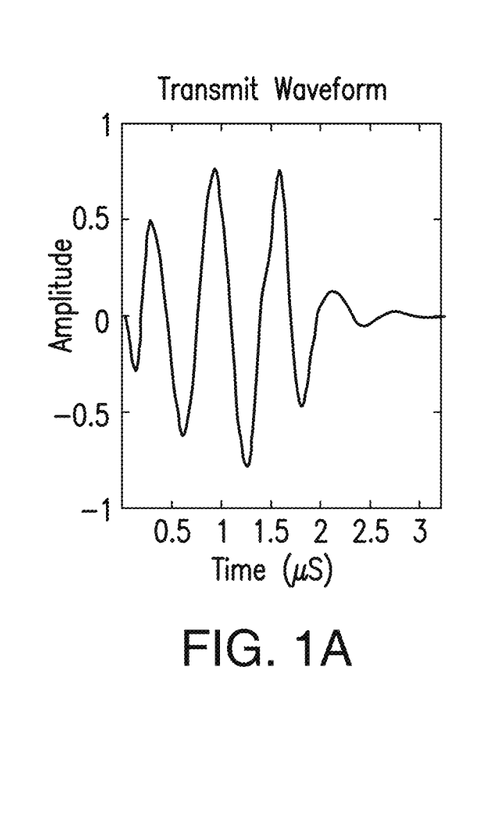
FIG. 1A provides properties of an example waveform in accordance with the disclosed subject matter FIG. 1B provides a graph showing an example focused transmit at a target focal spot in accordance with the disclosed subject matter.
Figure 1B:
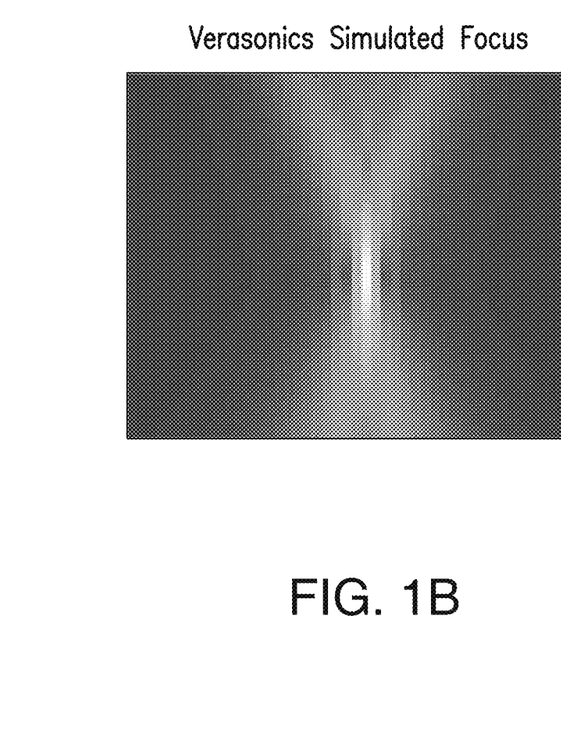

Theranostic Transducer: A Philips P4-1 phased array (e.g., Bandwidth: 1.5 MHz-3.5 MHz, Number of elements: 96) was connected to a Verasonics Vantage Ultrasound System. The P4-1 was programmed to transmit ~3 cycle pulses at 1.5 MHz (FIG. 1A). Time delays were calculated for each element to generate a focused transmit at the desired focal spot (FIG. 1B). These focused pulses were transmitted at a pulse repetition frequency (PRF) of 1,000 Hz. Between each focused transmit, power cavitation images were acquired.

Power Cavitation Imaging (PCI): Channel data was acquired between each focused transmits and beamformed using a delay-and-sum (DAS) beamforming algorithm. Additionally, the delays used in the DAS algorithm also took into account the appropriate time delays based on the focused transmits. An ensemble of n PCI images was accumulated over time and then spatiotemporally filtered using a singular value decomposition (SVD) filter. The SVD filter was crucial in order to remove stationary reflections (e.g., reflections from the skull) and slow-moving flow (e.g., tissue movement from breathing). Afterward, the power of the SVD filtered images was taken to generate a power cavitation image.

Phantom Experiments: Phantom experiments were carried out in a water bath filled with in-house-made polydispersed microbubbles (MB). The P4-1 was submerged in the MB bath, transmitting focused pulses at 1,000 Hz. After an ensemble of 1,000 PCI images was acquired (~1 second), SVD filtering was applied to the ensemble. A final cumulative PCI image was generated after the spatiotemporal filtering, representing the MB cavitation.

In vivo animal experiments: In vivo animal experiments were carried out in both wild-type C57BL/6 mice (N=4) and in the rhesus macaque monkey (N=1). In both animals, a burst of 100 transmits at a PRF of 1,000 Hz was used for focus transmits, equating to 100 PCI images acquired every burst. The burst repetition frequency was set to 0.5 Hz in order to allow bubble reperfusion in the brain between bursts. For mice, the estimated free field transmit negative peak pressure (PNP) was about 1.5 MPa, while in the NHP, the estimated free field transmit PNP was about 3.5 MPa.

Figure 2A:
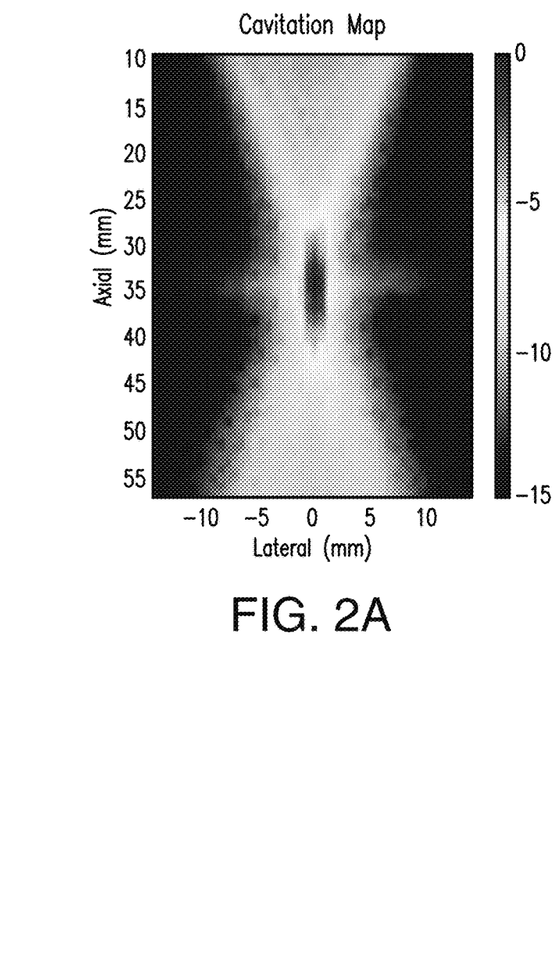
FIG. 2A provides a graph showing cumulative power cavitation in a water bath in accordance with the disclosed subject matter.

Power cavitation maps in bubble bath align well with hydrophone measurements: A cumulative power cavitation image of 1,000 frames was acquired in a water bath of MBs (FIG. 2A). The P4-1 was electronically focused to 35 mm, which matches well with the focus location seen in the power cavitation image. When compared to hydrophone measurements, axial and lateral cross-sections of the focus overlap well. The hydrophone measurement estimated the focus to be 12.4 mm axially and 1.2 mm laterally. The power cavitation image estimates the focus to be 7.9 mm axially and 1.7 mm.

Figure 3A:
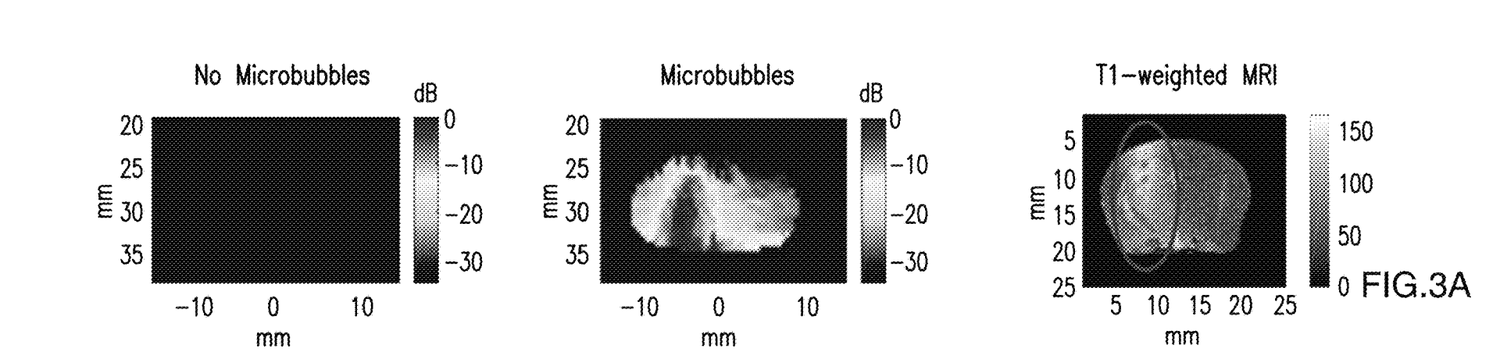
FIG. 3A provides example power cavitation images and contrast-enhanced MRI imaging in mice models with/without microbubbles in accordance with the disclosed subject matter.
Figure 3B:
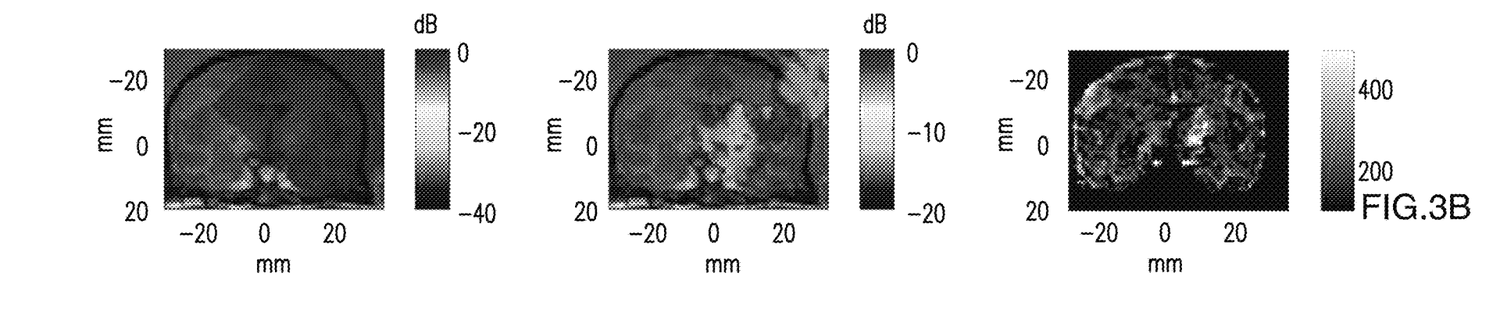
FIG. 3B provides example power cavitation images and contrast-enhanced MRI imaging in non-human primates (NHP) models with/without microbubbles in accordance with the disclosed subject matter.

In vivo animal experiments: Transcranial BBB opening using the P4-1 linear array was confirmed in both mice and NHP. For the mice (FIG. 3A), the power cavitation images revealed greater amounts of cavitation signal in the left hemisphere compared to the right hemisphere. Moreover, contrast-enhanced MRI images reveal contrast enhancement in a similar region of the brain. For the NHP (FIG. 3B), power cavitation images revealed detectable cavitation signals throughout the beam path, which correlated well with the contrast enhancement observed in the MRI. Within the beam focus, there is a 25.3 dB increase in signal intensity through the monkey skull after microbubbles are injected.

A P4-1 linear array (f0=2.5 MHz) connected to a Verasonics ultrasound system was used for both wild-type mice and non-human primates (NHP). A short, broadband 1.5 MHz pulse was electronically focused transcranially followed by active monitoring of microbubble cavitation using the same linear array. An ensemble of 100 transmits/receive pulses were transmitted at 1000 Hz every 2 seconds. Spatiotemporal clutter filtering was applied to each ensemble in order to isolate cavitation signals and generate 2D power cavitation images. BBB opening was confirmed using contrast-enhanced T1-weighted MRI imaging.

Transcranial BBB opening using the P4-1 linear array was confirmed in both mice and NHP. For the mice (FIG. 3A), the power cavitation images revealed greater amounts of cavitation signal in the left hemisphere compared to the right hemisphere. Moreover, contrast-enhanced MRI images reveal contrast enhancement in a similar region of the brain. For the NHP (FIG. 3B), power cavitation images revealed detectable cavitation signals throughout the beam path, which correlated well with the contrast enhancement observed in the MRI. Within the beam focus, there is a 25.3 dB increase in signal intensity through the monkey skull after microbubbles are injected. Further quantification is ongoing, including optimal parameters for safe and effective BBB opening and monitoring.

The disclosed subject matter provides techniques for both FUS-mediated BBB opening and cavitation monitoring using a single transducer. Power cavitation images generated using focused transmits in a water bath of MBs agree well with hydrophone measurements, demonstrating the feasibility of using a single theranostic transducer to excite microbubbles and to localize their cavitation using power cavitation imaging. The disclosed subject matter can be used for a human and/or animal subject. In both mice and NHP, transcranial power cavitation maps were able to be acquired during FUS-mediated BBB opening. In both animal models, contrast-enhanced T1-weighted MR images confirmed successful BBB opening using the theranostic transducer. Furthermore, a comparison between the transcranial power cavitation maps and the contrast-enhanced in MR images align well, liking the use of cavitation maps to localize BBB opening in vivo.

Example 2: Methods for a Single Transducer Capable of Cavitation Imaging and FUS-Induced BBB Opening The disclosed subject matter provides techniques for opening the BBB and cavitation imaging using a single low-frequency array. BBB opening efficiency and cavitation imaging is characterized using an off-the-shelf clinical transducer, which can be used for abdominal and cardiac imaging. This combination of BBB opening and cavitation imaging into one transducer is herein referred to as a theranostic transducer.

Theranostic Transducer: A P4-1 phased array (Fc: 2.5 MHz, Bandwidth: 1.5 MHz-3.5 MHz, number of elements: 96, Philips Healthcare, Bothwell, WA) was used. The P4-1 transducer was connected to Vantage 256 research ultrasound system (Verasonics Inc., Kirkland, WA.). The Vantage system was used to control the transducer and for data acquisition. The P4-1 was programmed to transmit ~3 cycle pulses at 1.5 MHZ. The transmits were focused to a predefined location by electronically delaying each element using the Vantage system.

Pressure field mapping of the P4-1 using a hydrophone: The pressure field mapping of the P4-1 was performed using a capsule hydrophone (HGL-0200, 200-μm aperture, Onda Corporation, Sunnyvale, CA). By fixing the location of the hydrophone and using a 3D positioning system to move the P4-1 transducer, the pressure field of the P4-1 can be acquired. Using a step size of 0.1 mm, the axial-lateral pressure profile of the P4-1 was acquired. The hydrophone measurements were converted to pressure field measured using the provided calibration factor by the manufacturer. Pressure field maps of the P4-1 were acquired for the 3-cycle focus transmits used throughout this aim.

Phantom experiments for Power Cavitation Imaging (PCI): Phantom experiments were conducted in a microbubble bath, where a small tank of de-ionized water with a mixture of microbubbles (approx. conc of 50,000 microbubbles/mL) was continually mixed with a magnetic stir bar. The P4-1 transmitted 3 cycles of focused pulses at a pulse repetition frequency (PRF) of 1,000 Hz. An ensemble of 1,000 frames were accumulate before being transferred to the host computer for beamforming and processing.

The power cavitation images were generated using the following data processing pipeline: a high-frame-rate acquired ensemble of raw data is accumulated on the Vantage system before it is transferred to the host computer. The number of raw frames acquired is set prior to the start of each experiment. Afterward, the data was transferred to the computer, and each raw frame was individually beamformed using a standard GPU-based delay and sum algorithm. The power doppler value of each pixel (I) within the final power cavitation image was calculated as:

$$I_{xy} = \frac{1}{N} \sum_{i=1}^{N} i_{xy}^2(N) \qquad (1)$$

where N is the number of frames acquired, and ixy is an array of pixel intensities across all acquires frames at that specific x-y coordinate within the beamformed frame.

Blood-brain barrier opening in mice: The transducer used for BBB opening. The P4-1 was used to open the BBB. A burst of 100, 3-cycle focused pulses were sent at a PRF of 1,000 Hz. These bursts of 100 pulses were sent at a burst repetition frequency (BRF) of 0.5 Hz. A total of 60 bursts were sent for a sonication duration of 2 minutes. The measured free-field peak negative pressure was estimated to be 1.5 MPa. A microbubble dose of 8E8 microbubbles/mL of the in-house made polydispersed bubble was injected prior to the start of sonication. Afterward, BBB opening was confirmed using the standard contrast-enhanced MRI imaging protocols.

Phantom experiments show the feasibility of cavitation imaging using a low-frequency array: The cavitation map generated in the microbubble bath can be seen in FIG. 2A. The transducer was electronically focused at an axial depth of 35 mm relative to the face of the transducer. The cavitation map is log compressed relative to the maximum intensity within the frame. From these maps, the strongest cavitation activity is occurring at around an axial depth of 35 mm and a lateral position of 0 mm, corresponding to the approximate location of the desired focusing location set by the Vantage system.

Figure 2B:
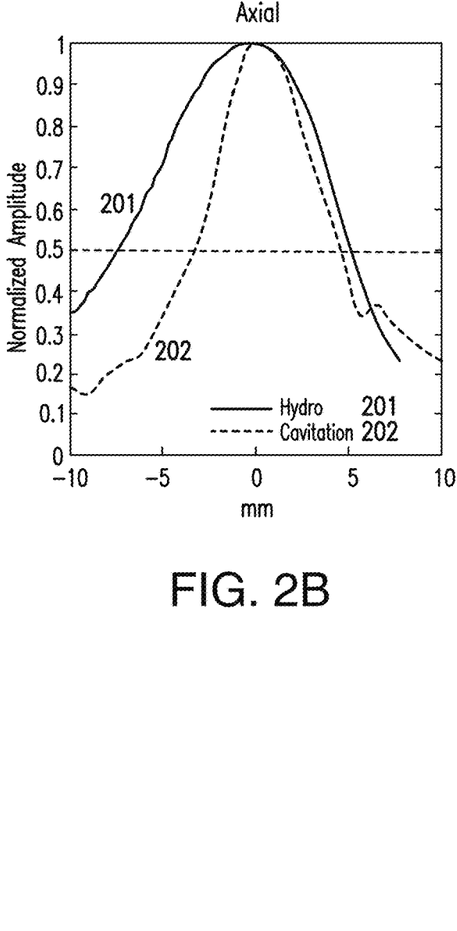
FIG. 2B provides a graph showing cross-sectional plots axial of the power cavitation image compared to measurements taken from a hydrophone.
Figure 2C:
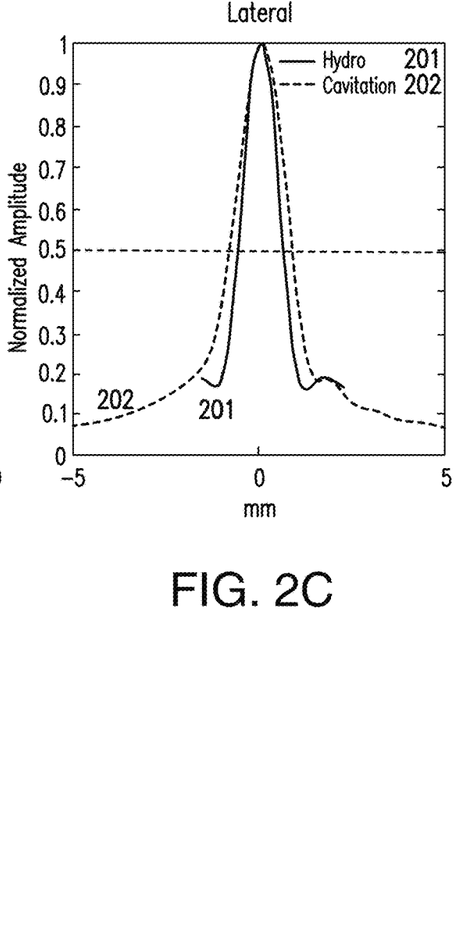
FIG. 2C provides a graph showing cross-sectional plots lateral of the power cavitation image compared to measurements taken from a hydrophone.

By imaging the cavitation of the microbubble bath, maps of the pressure field of the P4-1 are generated, as the strength of the microbubble cavitation is directly related to the pressure at the current location. As a result, using the P4-1 cavitation maps, the pressure field maps can be estimated and compared to measurements taken by a hydrophone. FIG. 2B compares the axial and lateral profiles acquired by a hydrophone 201 to the cavitation maps 202 generated. The full-width half max (FWHM) measurement of the P4-1 by the hydrophone was approximately 12.4 mm axially and 1.2 mm laterally. The estimated FWHM by the power cavitation maps were 7.9 mm axials and 1.7 mm laterally. The cavitation maps were in good agreement with the estimated pressure field, highlighting the feasibility of accurate cavitation imaging using a low-frequency array.

Figure 4A:
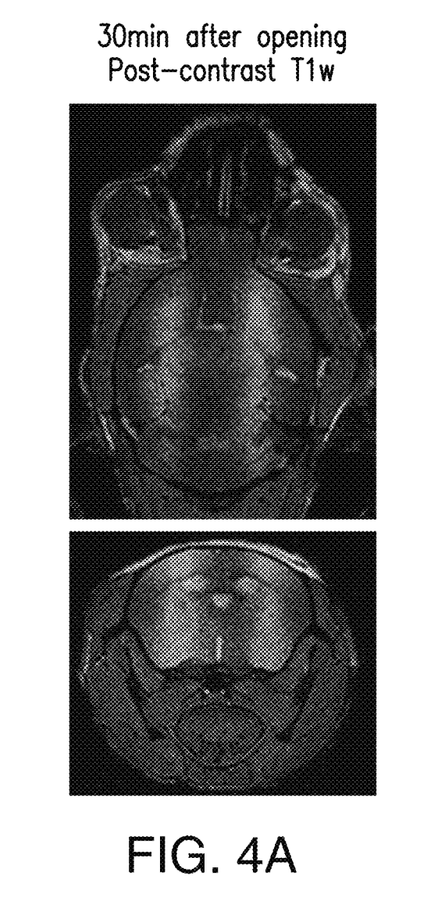
FIG. 4A provides example contrast-enhanced T1-weighted MRI images taken 30 minutes after sonication in accordance with the disclosed subject matter.
Figure 4B:
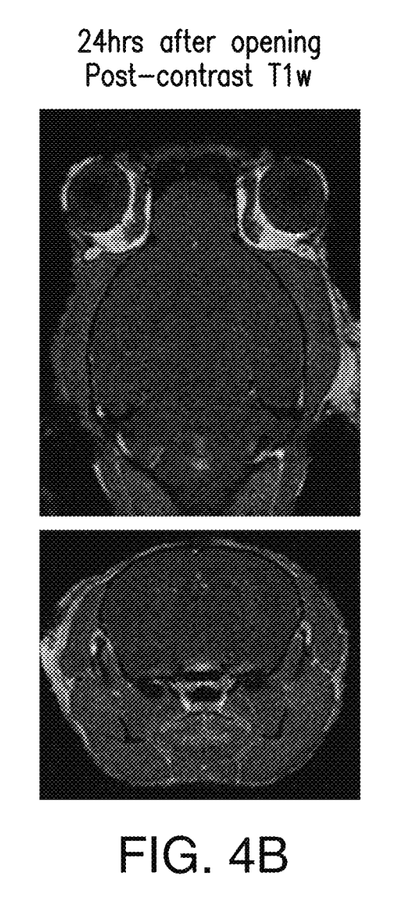
FIG. 4B provides example contrast-enhanced T1-weighted MIR images taken 24 hours after the BBB sonication in accordance with the disclosed subject matter.

Blood-brain barrier opening feasibility using the P4-1: Using the burst transmit scheme described above, BBB opening was successful in mice (FIG. 4A). Both the left and right hemispheres of the mice were sonicated consecutively, and contrast-enhanced T1-weighted MRI confirms opening in both hemispheres. Additionally, there was a lack of contrast enhancement in T1-weighted MRI, confirming closure of the ability for the P4-1 to create transient BBB openings (FIG. 4B).

BBB opening with the P4-1 was successful and shown to be transient using the sonication regime described above. The size of the opening seen in the coronal plane (FIG. 4B, bottom row) matches the opening size seen using the traditional FUS transducer described in previous aims, however, the size of the opening in the axial plane (FIG. 4B, top row) is much larger. The axial MRI reveals contrast enhancement across the entire mouse brain, even though only a single location was sonicated in each hemisphere. This difference in opening size is due to the fundamental capabilities of focusing by the linear array. The transducer can focus/steer the beam by electronically delaying when each individual element fires, changing the beams axial and lateral focus location. However, since the linear array is a 1D array of elements, it is unable to focus in the elevational direction, which is the direction along with each individual element. Focusing in the elevational direction is possible using a physical lens placed in front of the element during the production of the transducer, creating a fixed focus that cannot be changed. For the P4-1, a physical lens was used to focus in the elevational direction, with a focal spot at around 80 mm.

Example 3: Combined Blood-Brain Barrier Opening and Power Cavitation Imaging Using a Single Theranostic Transducer As shown in Examples 1 and 2, the P4-1 linear array, which is typically used for cardiac imaging, was shown capable of opening the BBB as well as imaging cavitation. The disclosed subject matter further provides algorithms to image cavitation during BBB opening, using a single theranostic transducer. The disclosed systems and methods can provide optimal imaging and opening in mice and non-human primates (NHPs). The disclosed subject matter can be used to predict BBB opening using cavitation maps.

The disclosed methods can combine cavitation imaging and BBB opening into a single sequence. The burst acquisition scheme can initially be implemented in vivo for both mice and NHPs. For example, a burst of 100, 3-cycle focused pulses can be sent at a PRF of 1,000 Hz. However, passive cavitation signals can be recorded between each transmitted pulse, capturing 100 frames of cavitation images per burst. The disclosed processing pipeline can be used to analyze the cavitation images and generate power cavitation images. These bursts of 100 frames can be transmitted at a burst repetition frequency (BRF) of 0.5 Hz. Exact parameters (e.g., number of pulses, PRF, BRF, etc.) can be optimized in vivo for this aim, with the goal of creating reliable transient openings without any damage. For example, pulse length can be increased (e.g., from 3 cycles to up to 20 cycles) for improved delivery of biologics through the opened BBB, but the power cavitation imaging resolution would suffer due to decreased axial resolution. Hematoxylin and eosin staining can be used to assess damage in mice brains. Due to the nature of NHP experiments, damage can only be assessed using MRI sequences for detecting edema and hemorrhage. Power cavitation images generated can be compared to contrast-enhanced MRI images to investigate the feasibility of using cavitation maps to predict BBB opening.

Example 4: A Low-Frequency Theranostic Linear Array for Clinical Translation to Humans The disclosed subject matter can provide a new low frequency theranostic linear array for applications in humans. A certain transducer can be operated at a center frequency of 1.5 MHz, a frequency range proven to be effective in opening the BBB in mice. The disclosed subject matter can be operated at the frequency for clinical use on humans. The biggest challenge ultrasound faces in the brain can be the human skull bone, which greatly attenuates and aberrates the ultrasound field as frequency increases. The disclosed subject matter can utilize a low-frequency theranostic array transducer at 500 kHz or lower to reach clinically relevant pressures through human skull fragments. The disclosed subject matter can also provide a clinical system for neuronavigation-guided FUS-induced BBB opening outside the magnetic bore to treat AD patients, using a spherically focused single element transducer at about 200–250 KHz.

The low-frequency theranostic array can have optimal specifications (e.g., frequency, number of elements, aperture, f-number, etc.) for a clinically relevant theranostic transducer. The Matlab toolbox known as k-Wave, an open-source acoustic modeling toolbox, can be used to simulate the different transducer configurations. Metrics to be assessed can include the transducer's focal size, point spread function, and attenuation through the human skull. Computed tomography (CT) scan of human skulls can be used in the simulation to assess the aberration and attenuation of the theranostic transducer's focus.

Once fabricated, the theranostic transducer can be characterized and evaluated through both ex vivo and in vivo experiments. The pressure field maps and focusing efficiency can be evaluated using hydrophone measurements. Phantom experiments using a microbubble flow chamber can be used to characterize the cavitation imaging capabilities. Specifically, different sized flow tube diameters and tube configurations can be used to assess the cavitation imaging resolution and sensitivity, respectfully. Additionally, phantom experiments with excised NHP and human skull fragments can be used to assess the transducer's transcranial performance.

In vivo assessments in NHP can be conducted to evaluate the transducer's capability for opening the BBB and imaging cavitation. The assessment can be performed in NHPs (e.g., Rhesus macaques (*Macaca mulatta*)). Each NHP can receive multiple sessions of therapy using the theranostic transducer, where different structures can be targeted. Contrast-enhanced T1-weighted MRI can be used to assess the opening location and size. Additionally, the contrast-enhanced T1-weighted MRI images can be compared to the cavitation maps acquired during the opening to assess their relationship. T2-weighted and susceptibility-weighted MRI can be acquired to assess the safety of the openings using the theranostic array (i.e., assess the presence of edema or hemorrhage).

Unless otherwise defined, all technical and scientific terms used herein have the same meaning as commonly understood by one of ordinary skill in the art. In case of conflict, the present document, including definitions, will control. Certain methods and materials are described below, although methods and materials similar or equivalent to those described herein can be used in the practice or testing of the presently disclosed subject matter. All publications, patent applications, patents, and other references mentioned herein are incorporated by reference in their entirety. The materials, methods, and examples disclosed herein are illustrative only and not intended to be limiting.

While it will become apparent that the subject matter herein described is well calculated to achieve the benefits and advantages set forth above, the presently disclosed subject matter is not to be limited in scope by the specific embodiments described herein. It will be appreciated that the disclosed subject matter is susceptible to modification, variation, and change without departing from the spirit thereof. Those skilled in the art will recognize or be able to ascertain using no more than routine experimentation, many equivalents to the specific embodiments described herein. Such equivalents are intended to be encompassed by the following claims.

What is claimed is:

1. A system for simultaneous blood-brain barrier opening and cavitation imaging, comprising:
    a transducer configured to
        generate a plurality of focused transmits, and
        obtain a plurality of power cavitation images corresponding to a detection of microbubble cavitation in response to the plurality of focused transmits, and
    a processor configured to
        control a parameter of the plurality of focused transmits,
        acquire the obtained plurality of power cavitation images, and
        generate a cavitation map based on the obtained plurality of power cavitation images;
    wherein the transducer is a single diagnostic transducer that is configured to obtain at least one power cavitation image between successive focused transmits.

2. The system of claim 1, further comprising a plurality of microbubbles.

3. The system of claim 2, wherein a size of the microbubbles ranges from about 1 micron to about 10 microns.

4. The system of claim 1, wherein the plurality of focused transmits comprises a focal depth between about 1 mm to about 100 mm.

5. The system of claim 1, wherein the plurality of focused transmits comprises a steering angle between about 0° to about 360°.

6. The system of claim 1, wherein the plurality of focused transmits comprises a pulse length between about 1 cycle to about 2500 cycles.

7. The system of claim 1, wherein the plurality of focused transmits comprises a center frequency between about 1.5 MHz to 3.5 MHz.

8. The system of claim 1, wherein the plurality of focused transmits comprises a pulse repetition frequency between about 100 Hz to about 1000 Hz.

9. The system of claim 1, wherein the processor is configured to adjust the parameter of each focused transmit to target multiple areas.

10. The system of claim 9, wherein the parameter is selected from the group consisting of a steering angle, a focal depth, a pulse length, a center frequency, a pulse repetition frequency, and combinations thereof.

11. The system of claim 1, wherein the processor is configured to perform microbubble power Doppler imaging.

12. The system of claim 11, wherein the transducer is configured to acquire microbubble power doppler images using a plane imaging wave between each of the focused transmit.

13. The system of claim 1, wherein the processor is configured to
    perform beamforming on the acquired images,
    accumulate beamformed images, and
    spatiotemporally filter the beamformed images using a singular value decomposition filter.

14. A method for simultaneous blood-brain barrier opening and cavitation imaging, comprising:

generating a plurality of focused transmits using a single therapeutic transducer configured to obtain at least one power cavitation image between each of the plurality of focused transmits;

simultaneously obtaining a plurality of power cavitation images using the therapeutic transducer, wherein the power cavitation images are obtained between each focused transmit and corresponded to a detection of microbubble cavitation in response to the plurality of focused transmits; and generating a cavitation map based on the power cavitation images.

15. The method of claim 14, further comprising adjusting a parameter of each focused transmit.

16. The method of claim 15, wherein the parameter is selected from the group consisting of a steering angle, a focal depth, a pulse length, a center frequency, a pulse repetition frequency, and combinations thereof.

17. The method of claim 14, further comprising:
introducing microbubbles; and
performing microbubble power Doppler imaging by acquiring microbubble power doppler images with a plane imaging wave between each of the focused transmit.

18. The method of claim 17, further comprising:
performing beamforming on the acquired images,
accumulating beamformed images, and
spatiotemporally filtering the beamformed images using a singular value decomposition filter.

19. The method of claim 17, wherein a size of the microbubbles ranges from about 1 micron to about 10 microns.

* * * * *